United States Patent [19]

Sheffield et al.

[11] Patent Number: 4,937,254
[45] Date of Patent: Jun. 26, 1990

[54] METHOD FOR INHIBITING POST-SURGICAL ADHESION FORMATION BY THE TOPICAL ADMINISTRATION OF NON-STEROIDAL ANTI-INFLAMMATORY DRUG

[75] Inventors: Warren D. Sheffield, Lebanon; Douglas B. Johns, Milford; Shalaby W. Shalaby, Lebanon, all of N.J.; Gere S. diZerega, Pasadena; LeRoy L. Richer, San Gabriel, both of Calif.

[73] Assignee: Ethicon, Inc., Somerville, N.J.

[21] Appl. No.: 148,464

[22] Filed: Jan. 26, 1988

Related U.S. Application Data

[63] Continuation-in-part of Ser. No. 900,122, Aug. 25, 1986, abandoned, which is a continuation-in-part of Ser. No. 802,545, Nov. 27, 1985, abandoned.

[51] Int. Cl.$^5$ .............................................. A61K 31/74
[52] U.S. Cl. ................................... 514/420; 514/576; 424/78
[58] Field of Search ................... 514/420, 576; 424/78

[56] References Cited

U.S. PATENT DOCUMENTS

| | | | |
|---|---|---|---|
| 3,755,558 | 8/1973 | Scribner | 424/47 |
| 4,141,973 | 2/1979 | Balazs | 514/54 |
| 4,166,800 | 9/1979 | Fong | 424/494 |
| 4,240,163 | 12/1980 | Galin | 623/6 |
| 4,337,251 | 6/1982 | Pfirrmann | 514/222.5 |
| 4,346,108 | 8/1982 | Singer | 424/317 |
| 4,389,330 | 6/1983 | Tice et al. | 424/497 |
| 4,427,649 | 1/1984 | Dingle et al. | 424/38 |
| 4,474,751 | 10/1984 | Haslam et al. | 424/78 |
| 4,474,752 | 10/1984 | Haslam et al. | 424/78 |
| 4,474,753 | 10/1984 | Haslam et al. | 424/78 |
| 4,478,822 | 10/1984 | Haslam et al. | 424/78 |
| 4,485,088 | 11/1984 | Chvapil | 424/447 |
| 4,517,295 | 5/1985 | Bracket et al. | 435/101 |
| 4,522,803 | 6/1985 | Lenk et al. | 424/1.1 |

OTHER PUBLICATIONS

Stangel et al., "Formation and Prevention of Postoperative Abdominal Adhesions", J. of Repro. Med., vol. 29, No. 3, Mar., 1984, pp. 143-156.

"The Cause and Prevention of Postsurgical Adhesions", diZerega, Pregnancy Research Branch, National Institute of Child Health and Human Development, National Institutes of Health, Bldg. 18, Rm. 101, Bethesda, MD 20205.

"Ibuprofen Inhibition of Postsurgical Adhesion Formation: A Time and Dose Response Biochemical Evaluation in Rabbits", Nishimura, Nakamura, and diZerega, Journal of Surgical Research 36, 115-124, Feb., 1984.

"Prevention of Postoperative Adhesions in Rabbits with Ibuprofen, A Nonsteroidal Anti-Inflammatory Agent", Siegler et al., Fertility and Sterility 34, No. 1, pp. 46-49, Jul., 1980.

"Prevention of Postoperative Peritoneal Adhesions with Ibuprofen", Bateman et al., Fertility and Sterility 38, No. 1, pp. 107-108, Jul., 1982.

"Oxyphenbutazone—Anti-Inflammatory Agent—in Prevention of Peritoneal Adhesions", Kapur et al., Arch Surg 98, pp. 301-302, Mar., 1969.

"The Use of Ibuprofen and Dexamethasone in the Prevention of Postoperative Adhesion Formation", O'-Brien, Obstetrics & Gynecology 60, No. 3, pp. 373-378, Sep., 1982.

"Biochemical Evaluation of Postsurgical Wound Repair: Prevention of Intraperitoneal Adhesion Formation with Ibuprofen", Nishimura et al., Journal of Surgical Research 34, pp. 219-226, 1983.

"The Carrier Potential of Liposomes in Biology and Medicine", New England Journal of Medicine, vol. 295, pp. 704-710 and pp. 765-770, Sep. 23 and 30, 1976.

Primary Examiner—Nathan M. Nutter

[57] ABSTRACT

Postsurgical adhesion formation is inhibited by the topical administration to the site of surgical trauma of a non-steroidal anti-inflammatory drug, preferably ibuprofen, suprofen, or tolmetin.

24 Claims, No Drawings

METHOD FOR INHIBITING POST-SURGICAL ADHESION FORMATION BY THE TOPICAL ADMINISTRATION OF NON-STEROIDAL ANTI-INFLAMMATORY DRUG

This application is a continuation-in-part of our copending application Ser. No. 900,122, filed Aug. 25, 1986 now abandoned, which was a continuation-in-part of application Ser. No. 802,545, filed Nov. 27, 1985 now abandoned.

The invention relates to a method for inhibiting post-surgical adhesion formation.

BACKGROUND OF THE INVENTION

Adhesion formation is a major post-surgical complication with no practical solution. The incidence of adhesion formation following surgery approaches 100 per cent, according to some sources, with a clinically significant complication rate of about 5 to 10 per cent, depending on the type of surgery. Among such complications are bowel obstruction, infertility, and pain. Occasionally, adhesions necessitate a second operative procedure to remove the adhesion, which may in turn further aggravate the problem.

Because of the seriousness of the problem, much medical research has been performed in efforts to find ways to combat adhesions. See, for instance, Stangel et al., "Formation and Prevention of Postoperative Abdominal Adhesions", the Journal of Reproductive Medicine,, Vol. 29, No. 3, Mar. 1984 (pages 143-156), and diZerega, "The Cause and Prevention of Postsurgical Adhesions", published by Pregnancy Research Branch, National Institute of Child Health and Human Development, National Institutes of Health, Building 18, Room 101, Bethesda, Md. 20205. Among the approaches that have been tried for preventing post-surgical adhesion are the following:

Systemic administration of ibuprofen (e.g., see Singer, U.S. Pat. No. 4,346,108);

Parenteral administration of antihistamines, corticosteroids, and antibiotics;

Intraperitoneal administration of dextran solution and of polyvinylpyrrolidone solution; and Systemic administration of oxyphenbutazone, a non-steroidal anti-inflammatory drug that acts by inhibiting prostaglandin production.

Corticosteroids have been administered intraperitoneally as well as systemically in efforts to prevent adhesions. (See the Stangel et al. article, cited above, on page 147, as well as the articles cited therein.) Some studies have questioned the efficacy of corticosteroids in adhesion prevention. In high doses, these materials may suppress the immune system and interfere with wound healing. Therefore, the use of corticosteroids does not seem to be an acceptable solution to the post-operative adhesion problem.

On the basis of the results of animal studies and limited human clinical studies, the systemic administration of non-steroidal anti-inflammatory agents such as ibuprofen (usually in combination with other medicaments such as antibiotics) appears to be the most efficacious pharmacological means now known to reduce the incidence of Post-surgical adhesions. An objection to this means is that relatively large amounts of the drug must be administered over a period of several days, thereby subjecting the patient to the significant risk of experiencing adverse side effects. Also, this means has been shown to be effective only in a limited number of types of surgical procedures, e.g., gynecological surgery. As reported by Nishimura, Nakamura, and diZerega (Journal of Surgical Research 36, 115-124, Feb. 1984), the minimum effective dose of systemically administered ibuprofen to inhibit postsurgical adhesion formation after abrasion or ischemia of the uterine horn of rabbits, is 70 mg/kg/day, administered once a day for at least 3 and preferably for 5 days post-operatively, with an additional dose 1 hour before surgery. In a similar series of experiments, Siegler et al. (Fertility and Sterility 34. No. 1, Jul. 1980, pages 46-49) found an effective dose of systemically administered ibuprofen to be about 21 mg/kg/day, administered three times daily (in three 7 mg/kg doses) for two days post-operatively, with the initial injection being given 30 minutes before surgery. The authors also reported that the best results were found in two rabbits that were each inadvertently given three extra 7 mg/kg doses. In order to deter adhesion formation in surgery to try to cure infertility, Corson et al. (The Journal of Reproductive Medicine, Vol. 29, No. 3, pages 143-156, Mar. 1984) recommend a regimen including systemically administered ibuprofen, 400 mg per dose three to four doses per day, starting the night of surgery and continuing to the fifth postoperative day. Assuming that the average woman weighs about 48 kg (110 pounds), this is a recommended dosage of 25 to 33 mg/kg/day. Singer, in U.S. Pat. No. 4,346,108, recommends a dosage of from about 2.5 to 50 mg/kg/day in single or divided doses, for ibuprofen administered systemically to combat adhesions.

BRIEF SUMMARY OF THE INVENTION

The invention comprises a method for inhibiting the formation of post-surgical adhesions in mammals (including humans) which method comprises the topical administration of a non-steroidal anti-inflammatory drug ("NSAID") to the site of surgical trauma.

THE PRIOR ART

The Singer patent, and the journal articles by Nishimura et al., Siegler et al., and Corson et al., all cited above, disclose the systemic administration of ibuprofen to combat adhesion formation.

Lenk et al., in U.S. Pat. No. 4,522,803, at column 17, lines 67 et seq., disclose phospholipid vesicles containing anti-inflammatory agents. Only steroid anti-inflammatory agents are specifically disclosed. No anti-adhesion utility is disclosed. A similar disclosure of phospholipid vesicles (liposomes) being used as carriers for anti-inflammatory steroid derivatives is found in Dingle et al., U.S. Pat. No. 4,427,649. The specific utility disclosed is the treatment of rheumatic disease such as arthritis.

Systemic administration of oxyphenbutazone to combat adhesions has been proposed. See, for example, Kapur et al., "Prevention of Reformation of Peritoneal Adhesions", Arch. Surg., Vol. 105, Nov. 1972, Pages 761-764.

U.S. Pat. No. 4,389,330 (Tice et al.) discloses the microencapsulation of pharmaceutically active agents in various materials, including lactide and glycolide polymers, and Scribner, in U.S. Pat. No. 3,755,558, discloses polylactide-drug mixtures for topical application. Among the drugs disclosed are "anti-inflammatories, such as hydrocortisone". (Col. 2, lines 28-29.)

Bracke et al., in U.S. Pat. No. 4,517,295 (Col 1, line 65-Col. 2, line 1), state that hyaluronic acid "might" be useful to combat post-surgical adhesions. Balazs, in U.S. Pat. No. 4,141,973, discloses anti-adhesion utility for a certain ultra-pure, high molecular weight fraction of hyaluronic acid.

DETAILED DESCRIPTION OF THE INVENTION

The pharmacologically active compositions that are employed in this invention are the non-steroidal anti-inflammatory drugs such as ibuprofen, tolmetin, indomethacin, sulindac, suprofen, oxyphenbutazone, naproxen, and pharmaceutically acceptable salts or esters thereof. NSAID's comprise a recognized class of compositions.

In accordance with the process of the invention, the active agent is applied topically to the site of surgical trauma in effective amounts for a period of time beginning after surgery and continuing for a period of time sufficient to inhibit the formation of post surgical adhesions. The active agent is preferably administered before significant wound healing has occurred. It is preferred and most convenient to administer the active agent in a "one-shot" application at the conclusion of the surgical procedure just prior to closing. However, in some cases it may be desired to administer the active agent continually over a period of time, as would be the case if the active agent were administered by a catheter or in a sustained release formulation. The specification, below, describes some methods that can be used to determine the optimum periods of administration when the mode of application is continual, as by catheterization (in the animal models used, an implanted osmotic mini-pump was used—this procedure is analogous to catheterization in a human). However, the most convenient mode of administration is via a single dose application of the active agent at the conclusion of the surgical procedure, just prior to closing, as is illustrated below in certain of the examples.

By the term "topically", is meant that the NSAID is administered non-systemically to the surface of the tissue (internal or, in some cases, external) to be treated. The treatment is intended to be "locally effective", that is, the treatment is intended to affect only the tissue treated or adjacent or neighboring tissue. The term "site of surgical trauma" is meant to include the site of tissue that has been injured in any way, and includes, for example, tissue sites that have undergone incision, drying, suturing, excision, abrasion, contusion, laceration, anastomosis, manipulation, prosthetic surgery, curettage, orthopedic surgery, neurosurgery, cardiovascular surgery, or plastic or reconstructive surgery. "Site of surgical trauma" also includes tissue that is adjacent to the injured tissue. In some cases, effective treatment may be obtained simply by the topical treatment of an NSAID to tissue near that which has been surgically manipulated.

The method of the invention is useful in any surgical procedure in which it is desired to inhibit the formation of post-surgical adhesions. It is thus broadly useful in all types of surgery in which adhesion formation can be a complication. For instance, the invention is useful in abdominal surgery, in gynecological surgery, in thoracic surgery, in orthopedic surgery affecting tendons, ligaments, etc., in neurological surgery affecting the dura mater, and the like.

The NSAID may be administered to the site of surgical trauma by any convenient mode such as, for example, by lavage, by catheter, by coating directly on the site in a salve, ointment, gel, cream, aqueous surface active composition, emulsion, suspension, film, or foam, or by any other convenient mode. The site can be contacted directly, as by applying a salve, ointment, gel, etc., or in some cases the medicament can be introduced to a site near the site of trauma and natural migration of fluids will serve to carry the medicament to the desired site. Such natural migration of fluids can occur, for instance, intraperitoneally, in response to peristaltic contraction of the intestines.

The NSAID is ordinarily administered in a sterile formulation in a pharmaceutically acceptable carrier or vehicle such as phosphate buffered saline ("PBS"), isotonic saline, purified water, an organic carrier (which may be in an aqueous solution or suspension) such as hyaluronic acid or a derivative thereof or a similar polysaccharide such as chitosan or a derivative thereof, a lipid, for example, an aqueous phospholipid composition, which may be in the form of a phospholipid vesicle (liposome) or it may be simply a mixture of a phospholipid in water, dextran, polymers such as p-dioxanone, lactide, and/or glycolide based absorbable polymers or polyacrylamide (the polymer/NSAID formulation may be in the form of polymeric microcapsules containing the NSAID or it may be in the form o>a salve- or ointment-like formulation or a gel or gel-like composition), or in an aqueous solution of a surfactant such as a polyoxyethylene-polyoxypropylene block coPolymer or a sorbitan fatty acid ester-polyoxyethylene ether. Sterilization of the formulation may be accomplished in the usual ways, including aseptic preparation, filtration, exposure to gamma radiation, autoclaving, and the like.

A general procedure for preparing a polymeric microcapsule containing a drug, and which is applicable to incorporating NSAID's in polymeric microcapsules, is the following:
1. The drug and the polymer are dissolved in a volatile organic solvent;
2. The solvent containing the drug and polymer is dispersed in water with a dispersing agent;
3. The organic solvent is evaporated from the dispersion product of step 2, either by mild heating or by vacuum evaporation, or by a combination of the two; and
4. The resulting microcapsules are recovered from the aqueous dispersion by customary procedures such as filtration, centrifugation, or the like, usually coupled with one or more washing steps.

This procedure is illustrated for this invention in Examples 1, 2, 9, and 10, below:

EXAMPLE 1

(a) To a small vial was added 9.39 grams of poly(lactide-co-glycolide-65:35) ("PLG"—a 65/35, by weight, copolymer of lactide and glycolide having an inherent viscosity in chloroform of 0.5 dl/g), 0.75 gram refined sesame seed oil, 1.140 grams ibuprofen ("IBF"), and 40 ml of dichloromethane ("MeCl$_2$"). The solution obtained was added to 400 ml of aqueous 5% wt/vol poly(vinyl alcohol) ("PVA"—Air Products Vinol Grade 523) in a one liter resin kettle equipped with a mechanical stirrer and vacuum take off, which was being cooled in an ice/water bath and stirred at 500 rpm. After allowing 10 minutes for emulsification, vacuum was slowly applied by means of an aspirator to an absolute pressure of 500 mm of mercury over 1.5 hours. The vacuum was then maintained for an additional 19.5 hours (to remove the MeCl$_2$ solvent), at which time vacuum and stirring was stopped and the contents of the flask was poured into a one liter beaker and diluted to 800 ml total volume with water. (An alternative method for removing the MeCl$_2$ solvent is to heat at 30° C. for two hours at atmospheric pressure.) The contents of the beaker were added to centrifuge tubes and they were centrifuged at about 1000 rpm for two minutes. The liquid was decanted, fresh water was added, and centrifugation was repeated. This procedure was repeated one more time, and after the third wash, the last traces of water were removed by freeze drying. The dried sample was a free flowing white powder which weighed 2.03 grams. The powder was examined at 100X magnification with an optical microscope and was found to contain microcapsules which ranged in size from about 1 to 10 microns. No free drug crystals were noted. Subsequent NMR analysis indicated that 8.6 wt. % IBF was present.

(b) To make control microcapsules, the foregoing procedure is repeated without adding the IBF.

(c) Microcapsules produced as described above, both with and without IBF, are dispersed in an aqueous dispersion of lecithin in proportions of 1.5 grams of microcapsules per 50 ml of 0.05 weight per cent aqueous lecithin. After freeze drying, 1.4 grams of microcapsules are obtained which contain about 1.4 weight per cent of lecithin.

EXAMPLE 2

To a small vial was added 1.50 grams of PLG, 0.50 gram IBF, and 5 ml of MeCl$_2$. The resulting solution was added to 50 ml of 3% aqueous PVA solution which was being cooled in an ice/water bath and stirred at 500 rpm. Vacuum was applied as before and after washing and freeze-drying, 1.100 grams of microcapsules was obtained. The microcapsules ranged in size from 10 to 120 microns and were found to contain 17.1% by weight IBF by NMR.

EXAMPLE 3

IBF/PLG microcapsules (Example 2) which were found to contain 17.1% by weight IBF (NMR) were investigated. In five separate 4 ounce amber jars was placed 100 mg of microcapsules and 100 ml of pH 7.27 phosphate buffer. The caps were tightly closed and the jars incubated at 37° C., with no agitation. After 15 minutes, 1 day, 2 days, 7 days, and 14 days, a jar was removed, the microcapsules collected by filtration, washed well with water, dried under vacuum, and analyzed for IBF content by NMR. The results shown in the attached table indicate that approximately 50% of the drug was released in the first 7 days and the remainder was completely released by day 14. (Negligible polymer weight loss occurred over the 14 day period.)

TABLE I

In Vitro Release of IBF From PLG Microcapsules

| Sample | Time (Days) | WT % IBF REMAINING (% of TOT CAPSULE WT) |
|---|---|---|
| 1 | 0 | 17.0 |
| 2 | 1 | 14.3 |
| 3 | 2 | 13.6 |
| 4 | 7 | 10.0 |
| 5 | 14 | 0.0 |

Methods for incorporating drugs in lipid carriers are known in the art. For instance, one procedure for encapsulating a drug in a phospholipid vesicle (liposome) is the following:

a lipid or mixture of lipids such as lecithin or other phospholipid, which may be mixed with cholesterol or other lipoid substance, is dissolved in an organic solvent such as diethyl ether; and an aqueous phase containing the material to be encapsulated (in this case, an NSAID) is added to the lipid solution, and the mixture is agitated as by exposing it to ultrasonic sound waves (sonicated). Preferably, the organic solvent is removed during sonication, as by use of heat or vacuum or both, although in some cases the solvent can be removed after the sonication. This procedure typically produces a unilamellar vesicle.

Another procedure for producing a phospholipid vesicle (in this case a multilamellar vesicle—"MLV") containing a medicament is to form a film of dry lipid, as by evaporating the solvent from an organic solvent solution containing a lipid to form a film on the walls of the vessel containing the starting solution, and then stirring in the aqueous phase containing the NSAID to be encapsulated. (The evaporation can be done by spray drying or by vacuum evaporation, or by any other convenient method.) Free unencapsulated NSAID can be separated from MLV's by centrifugation at, e.g., 12,000 rpm.

Preferably, the vesicle containing the NSAID is dehydrated, as by freeze drying, after preparation, in order to insure long term storage stability. The aqueous vesicle suspension can be reconstituted just prior to use by adding sterile phosphate buffered saline, sterile water, or the like.

The use of MLV's of comparatively large size (e.g., from about 1 to about 5 microns) appears to be preferable in order to increase the dwell time of the vesicle containing the NSAID in the peritoneal cavity (or other body cavity). It is also preferred to use a pure or synthetic phosphatidylcholine in which the fatty acid moieties in the phosphatidylcholine molecule are derived from a single fatty acid, in preparing the vesicle instead of natural lecithin, which is ordinarily a mixture of compounds. Example 13, below, illustrates the preparation of a multilamellar vesicle containing an NSAID.

The following United States patents describe the preparation, by various procedures, of phospholipid vesicles containing various medicaments:

Lenk et al. No. 4,522,803
Baldeschwieler et at. No. 4,310,505
Mezei et al. No. 4,485,054
Gersonde et al. No. 4,452,747
Kelly No. 4,356,167
Papahadjopoulos et al. No. 4,241,046
Suzuki et al. No. 4,016,100
Sache et al. No. 4,239,754
MacDonald No. 4,532,089
Rahman et al. No. 3,993,754

See also Callahan et al., European patent application No. 0126580, published Nov. 28, 1984, and Gregoriadis, "The Carrier Potential of Liposomes In Biology and Medicine", New England Journal of Medicine, Vol. 295, pp. 704-710 and pp. 765-770 (Sept. 23 and 30, 1976).

The foregoing are incorporated herein by reference as general procedures which can be utilized for the incorporation of NSAID's in liposomes.

Other procedures for incorporating drugs in phospholipids (simple aqueous mixtures such as micellar dispersions or liposomes), and which are applicable to NSAID's, are described in Sears, U.S. Pat. Nos. 4,426,330 and 4,145,410, and Sears et al., U.S. Pat. No. 4,298,594, the disclosures of which are incorporated herein by reference. See also the disclosure beginning at Example 18, below.

It is not essential that the NSAID medicament used in the invention be encapsulated in an inside compartment or compartments of the carrier as will normally be the case when the carrier is a phospholipid vesicle. In some cases it is acceptable for the NSAID to be dissolved or otherwise distributed throughout the carrier or vehicle.

The non-steroidal anti-inflammatory drug is delivered to the site of surgical trauma in effective quantities over the desired period of time, which period may vary from patient to patient, with the type or severity of the trauma, with the location of the traumatized tissue in the body, with the nature of the NSAID or the carrier, or the like. It has been found that in many cases the NSAID need be administered only during the initial stages of the wound healing process, and therefore the duration of the administration in such cases may only be a few hours, e.g., as short as from about one to three hours. In other cases, the duration of administration may be from about one or two and up to five days, and in some cases up to seven days or more, post-operatively. The examples below illustrate procedures for determining the order of magnitude of effective quantities of the drug and the period of time over which the drug is administered for effective results.

The following studies use rabbit models to illustrate the adhesion inhibition effectiveness of the topical administration of a non-steroidal anti-inflammatory drug to the site of surgical trauma:

EXAMPLE 4

New Zealand white female rabbits (1.8–2.0 kg) underwent midline laparotomy using acelepromazine and ketamine anesthesia. A 3×5 cm abrasion was produced over the right-lateral peritoneal side-wall by scraping the surface peritoneum with a scalpel until punctate bleeding developed over the entire 3×5 cm area. A second abrasion covering the same total area (15 cm$^2$) using the same technique was developed 1.5–2.0 cm inferior to the initial site along the right-lateral peritoneal side-wall. This second site was used as an untreated control. The serosal surface of the large bowel adjacent to the peritoneal abrasion sites was also similarly abraded.

IBF contained in PLG microcapsules produced as described in Example 1, were suspended in 15 weight per cent aqueous poly(vinyl pyrrolidone) "PVP" (GAF Povidone C-15). The proportions were 15 grams of microcapsules per 100 grams of the PVP solution.

The lecithin-containing microcapsules were used in half of the experiments. The suspension was dripped on the wound in an amount such that about 40 mg of IBF (about 470 mg of microcapsules) was applied to the wound site. One control was the PVP solution containing IBF-free microcapsules, and the other was the PVP solution containing IBF-free microcapsules with lecithin.

Seven days after the day of abrasion, the rabbits were sacrificed by pentobarbital overdose. The extent of adhesions was evaluated as follows:
1. No adhesions
2. Filmy adhesions (separable)
3. Mild adhesions (not separable—covering up to about 35% of the test area)
4. Moderate adhesions (not separable—covering about 35 to 60 % of the test area)
5. Severe adhesions (not separable—covering greater than about 60% of the test area)

The evaluation ratings set forth above are useful in the context of comparing the efficacy of various means for inhibiting the formation of adhesions. A rating of "1" is the objective, since clinical complications can result from even mild adhesions, although such complications are considered to be more likely to occur with severe adhesions than with mild or moderate adhesions.

The following Table II presents the results:

TABLE II

| Rabbit No. | Ibuprofen | Lecithin | Evaluation Ibuprofen Treatment | Evaluation Untreated Controls |
|---|---|---|---|---|
| 1 | yes | no | 4 | 4 |
| 2 | yes | no | 4 | 5 |
| 3 | yes | no | 1 | 1* |
| 4 | yes | yes | 3 | 5 |
| 5 | yes | yes | 4 | 5 |
| 6 | yes | yes | 3 | 5 |
| 7 | no | no | 5 | 5 |
| 8 | no | no | 5 | 5 |
| 9 | no | no | 5 | 5 |
| 10 | no | yes | 5 | 5 |
| 11 | no | yes | 5 | 5 |
| 12 | no | yes | 5 | 5 |

*The surgical procedure followed in this experiment induces adhesion formation in about 87 percent of untreated rabbits. Evidently this rabbit was one of the approximately 13 percent that do not develop adhesions.

The results indicate some anti-adhesion activity exhibited by the microcapsules containing ibuprofen.

It is relevant to note that when the vehicle control site is in the same rabbit as the test site, migration of fluid in the peritoneal cavity can carry some of the medicament from the NSAID treatment site to the vehicle control site. Therefore, it is possible that the untreated (by "untreated" is meant no active medicament) control sites of rabbits Nos. 1–6 in Table II and analogous untreated control sites reported below could have received small amounts of NSAID owing to migration or circulation of fluid within the peritoneal cavity. However, if any of the untreated control sites did receive some of the active medicament by such fluid migration, it would have been significantly less than that received at the treatment site in the same rabbit. Therefore, differences in results between the treatment sites and the control sites in the same rabbit can confidently be interpreted as being caused by the adhesion inhibition effect of the NSAID.

EXAMPLE 5

In order to carry out dose response studies and time response studies, miniature osmotic pumps (Alzet mini pumps, model 2M1L or model 2002—these pumps are described in Higuchi et al., U.S. Pat. No. 3,995,631) were used to deliver the anti-adhesion agent in a continuous stream at a very low, controlled flow rate, to the site of the surgical trauma in the test rabbits over a period of time, up to seven days. The mini-pumps therefore deliver the medicament in a manner analogous to a catheter delivery mode.

New Zealand white female rabbits (1.8 to 2.0 kg) underwent midline laparotomy using acelepromazine and ketamine anesthesia. A 3×5 cm flap of parietal peritoneum (about 1 mm thick) was sharply dissected from the right lateral peritoneal side-wall. The serosal surface of the adjacent large bowel was abraded with a scalpel until punctate bleeding developed. This area between the excised parietal peritoneum and adjacent large bowel serosa was then used for evaluating the efficacy of the test medicament for adhesion inhibition. A second excision of parietal peritoneum covering the same total area (about 15 cm$^2$) was performed 1.5 to 2.0 cm inferior to the initial test site along the right lateral peritoneal side-wall. Abrasion of the adjacent large bowel serosa was performed as described above for the treatment site. This second area was used to determine the effectiveness of the surgical procedure in producing adhesions and the response to vehicle controls.

Alzet mini pumps containing ibuprofen dissolved in phosphate buffered saline ("PBS") were sewn into the right dorsal subcutaneous space of the test rabbit with VICRYL (Polyglactin 910) sutures placed 3 to 5 mm from each end of the pump. The polyethylene catheter tip leading from the pump into the peritoneal cavity of each rabbit was placed 2 to 3 mm over the injury test site. The catheter was secured in place by two 3/0 VICRYL sutures which did not involve the site of the injury. A similar pump and catheter system containing PBS vehicle only was implanted in the middle portion of the inferior (vehicle control) abrasion site.

Two different mini pumps were used in these experiments. The first (a 2 ml pump) had a pumping rate of 10 microliters per hour and the second (a 0.2 ml pump) had a pumping rate of 0.5 microliter per hour. Each pump contained phosphate buffered saline (pH=7.2, unless otherwise indicated), 2 ml in the larger pump and 0.2 ml in the smaller pump. The control pumps contained PBS alone, and the treatment pumps contained either 20 mg of IBF (2 ml pump) or 2 mg of IBF (0.2 ml pump).

The results seven days after the operation were as shown below in Table III. The evaluation procedure was the same as the one described in Example 4.

TABLE III

| Rabbit No. | Pump Size | Evaluation Ibuprofen Treatment | Vehicle Control |
| --- | --- | --- | --- |
| 1 | 0.2 ml | 5 | 5 |
| 2 | 0.2 ml | 4 | 5 |
| 3 | 0.2 ml | 4 | 5 |
| 4 | 2 ml | 4 | 5 |
| 5 | 2 ml | 2 | 5 |
| 6 | 2 ml | 1 | 5 |

The smaller of the two pumps gave a slight positive response in two of three rabbits, whereas the larger pump gave significant positive responses in two out of three rabbits and a slight positive response in the other.

EXAMPLE 6

In order to try to better define the threshold dosage rate for ibuprofen in this experimental model, similar experiments were carried out with the two sizes of pumps, using different concentrations of IBF per pump. Table IV, below, sets forth the concentrations of IBF per pump and responses in this series of experiments:

TABLE IV

| Rabbit No. | Pump Size | Concentration of IBF, mg/ml | Evaluation Treatment | Vehicle Control |
| --- | --- | --- | --- | --- |
| 1 | 0.2 ml | 10 | 1 | 4 |
| 2 | 0.2 ml | 10 | 4 | 5 |
| 3 | 0.2 ml | 10 | 5 | 5 |
| 4 | 2 ml | 10 | 3 | 5 |
| 5 | 2 ml | 10 | 4 | 4 |

TABLE IV-continued

| Rabbit No. | Pump Size | Concentration of IBF, mg/ml | Evaluation Treatment | Vehicle Control |
| --- | --- | --- | --- | --- |
| 6 | 2 ml | 10 | 3 | 5 |
| 7 | 0.2 ml | 3 | 4 | 5 |
| 8 | 0.2 ml | 3 | 5 | 5 |
| 9 | 0.2 ml | 3 | 4 | 5 |
| 10 | 2 ml | 3 | 3 | 5 |
| 11 | 2 ml | 3 | 5 | 5 |
| 12 | 2 ml | 3 | 4 | 5 |
| 13 | 0.2 ml | 1 | 5 | 5 |
| 14 | 0.2 ml | 1 | 5 | 5 |
| 15 | 0.2 ml | 1 | 1 | 4 |
| 16 | 2 ml | 1 | 5 | 5 |
| 17 | 2 ml | 1 | 5 | 5 |
| 18 | 2 ml | 1 | 4 | 5 |
| 19 | 0.2 ml | 0.3 | 5 | 5 |
| 20 | 0.2 ml | 0.3 | 5 | 5 |
| 21 | 0.2 ml | 0.3 | 5 | 5 |
| 22 | 2 ml | 0.3 | 5 | 5 |
| 23 | 2 ml | 0.3 | 5 | 5 |
| 24 | 2 ml | 0.3 | 4 | 5 |

This series of experiments indicates that, in this rabbit model and particular mode of delivery, the threshold dosage at which significant anti-adhesion effects began to be noted occurred when pumps containing concentrations between 1 and 3 mg of IBF per ml were used. No significant difference was noted here between the two different sized pumps.

An effective dose of a topically applied drug is often expressed in terms of concentration of the drug in the carrier or vehicle, coupled with the number of times per day the drug is applied. In the present invention, the effective dose will be dependent upon factors such as nature of specific NSAID used, nature of carrier or vehicle, nature of tissue to be treated, type, severity, and location of trauma, and mode of delivery (i.e., continuous delivery by catheter or a one-time application). Therefore, no hard and fast rule can be formulated that will apply in all cases, and experiments analogous to those reported in this Example 6 will have to be performed in order to precisely define the threshold dosage for each different NSAID, for specific carrier or vehicle systems, and for specific modes of delivery. It is well within the ability of the person skilled in the art to carry out the necessary experiments to determine threshold dosages, after having read this disclosure.

EXAMPLE 7

In order to determine the time period over which the anti-adhesion agent is administered in order to demonstrate significant anti-adhesion effect in the rabbit model used in this series of experiments using the Alzet mini pump as the mode of administration, the following series of experiments were carried out (using the experimental procedure described above in Example 5):

The 2 ml pump was used containing 10 mg/ml of IBF, and the catheter delivering the treatment solution to the site of the surgical trauma was disconnected 1, 2, 3, 4, and 5 days post-operatively. The rabbits were sacrificed 7 days post-operatively, and evaluated as above. The results are displayed in Table V, below.

TABLE V

| Rabbit No. | Post-Op Day Catheter Disconnected | Evaluation Ibuprofen Treatment | Vehicle Control |
| --- | --- | --- | --- |
| 1 | 1 | 5 | 5 |
| 2 | 1 | 4 | 4 |

TABLE V-continued

| Rabbit No. | Post-Op Day Catheter Disconnected | Evaluation Ibuprofen Treatment | Vehicle Control |
|---|---|---|---|
| 3 | 1 | 3 | 1 |
| 4 | 2 | 4 | 4 |
| 5 | 2 | 5 | 5 |
| 6 | 2 | 1 | 1 |
| 7 | 3 | 4 | 1 |
| 8 | 3 | 1 | 3 |
| 9 | 3 | 1 | 3 |
| 10 | 4 | 4 | 5 |
| 11 | 4 | 3 | 1 |
| 12 | 4 | 1 | 1 |
| 13 | 5 | 3 | 5 |
| 14 | 5 | 4 | 5 |
| 15 | 5 | 5 | 5 |

With IBF, in this model, it appears that administration of the NSAID via the 2 ml mini pump in PBS for at least three days is required in order for the drug to have significant anti-adhesion effects. With other NSAID's and/or other delivery modes, and with other types of surgical trauma or with trauma of differing severity or in other locations in the body, it is reasonable to expect that the minimum period of time will differ. In any given case, the minimum period of time over which the NSAID must be administered when it is administered continually as by a catheter or an implanted mini pump as in this Example 7, can be determined by experiments analogous to that described in this Example.

The NSAID active ingredient is administered to the site of surgical trauma topically. Such topical administration can be by spraying, lavage, dripping on the site, by catheter administration, or the like. The exact method of administration chosen has not been found to be critical, as long as an effective dose is administered over the period beginning before significant wound healing has occurred and continuing for at least the initial stages of wound healing. As will be illustrated in later Examples, a single application of the active agent can show efficacy in many cases. With such single applications, the time period over which the active agent is in effective contact with the site of surgical trauma may be very short, e.g., as little as, for example, about one to three hours. When the method of the invention is carried out by a single application of the active agent, the most convenient time for such administration is just prior to closing at the end of an operative procedure.

EXAMPLE 8

By a procedure analogous to that described above in Example 5, the 2 ml Alzet mini pump was used to deliver suprofen to the test site in the rabbits. The concentration of suprofen was 2.5 mg/ml of PBS (pH=7.4). The rabbits were sacrificed 7 days post-operatively, and evaluated as above. The results are set forth in Table VI, below:

TABLE VI

| | 2.5 mg/ml Suprofen | |
|---|---|---|
| | Evaluation | |
| Rabbit No. | Suprofen Treatment | Vehicle Control |
| 1 | 3 | 4 |
| 2 | 4 | 3 |
| 3 | 3 | 5 |
| 4 | 4 | 5 |
| 5 | 4 | 4 |

TABLE VI-continued

| | 2.5 mg/ml Suprofen | |
|---|---|---|
| | Evaluation | |
| Rabbit No. | Suprofen Treatment | Vehicle Control |
| 6 | 3 | 5 |
| 7 | 3 | 4 |

EXAMPLE 9

To a small vial was added 2.78 grams of PLG, 0.30 gram suprofen, and 8 ml of $MeCl_2$. The resulting solution was added to 120 ml of 3% aqueous PVA solution which was heated to 30° C. while being mechanically stirred at 500 rpm. After two hours, the microcapsules were isolated as described in Example 1, and after washing and freeze-drying, 1.61 grams of microcapsules were obtained. The microcapsules ranged in size from about 10 to 250 microns and were found to contain 7.0% by weight suprofen by NMR.

EXAMPLE 10

To a small vial was added 1.25 grams of poly(D,L-Lactic acid), 0.12 grams refined sesame seed oil, 0.152 gram IBF, and 3 ml of $MeCl_2$. The resulting solution was added to 30 ml of 3% aqueous PVA solution which was being cooled in an ice/water bath and stirred at 500 rpm. Vacuum was applied as described in Example 1, and after washing and freeze-drying, 1.12 grams of microcapsules were obtained. The microcapsules ranged in size from 10 to 75 microns and were found to contain 8.7% by weight IBF by NMR.

EXAMPLE 11

By a procedure similar to that described above in Example 5, the 2 ml mini pump was used to deliver varying quantities of suprofen sodium (i.e., the sodium salt of suprofen) to the rabbit model. The quantities of medicament contained in the PBS (pH=6.9) varied from 0.03 mg/ml to 3.0 mg/ml. The rabbits were sacrificed seven days post-operatively and evaluated as above. The results are set forth below in Table VII:

TABLE VII

| | Suprofen, Dosage Response Studies | | |
|---|---|---|---|
| | Concentration of Suprofen, mg/ml | Evaluation | |
| Rabbit No. | | Treatment | Vehicle Control |
| 1 | 3 | 1 | 1 |
| 2 | 3 | 1 | 1 |
| 3 | 3 | 1 | 1 |
| 4 | 3 | 4 | 4 |
| 5 | 3 | 1 | 1 |
| 6 | 1 | 4 | 5 |
| 7 | 1 | 1 | 1 |
| 8 | 1 | 3 | 4 |
| 9 | 1 | 1 | 5* |
| 10 | 1 | 1 | 3 |
| 11 | 0.3 | 1 | 5 |
| 12 | 0.3 | 3 | 4 |
| 13 | 0.3 | 3 | 5 |
| 14 | 0.3 | 3 | 3 |
| 15 | 0.3 | 3 | 4 |
| 16 | 0.1 | 3 | 3 |
| 17 | 0.1 | 3 | 4 |
| 18 | 0.1 | 3 | 5 |
| 19 | 0.1 | 1 | 5 |
| 20 | 0.1 | 5 | 5 |
| 21 | 0.03 | 5 | 1 |
| 22 | 0.03 | 1 | 1 |
| 23 | 0.03 | 4 | 4 |

TABLE VII-continued

| | Suprofen, Dosage Response Studies | | |
|---|---|---|---|
| | Concentration of Suprofen, | Evaluation | |
| Rabbit No. | mg/ml | Treatment | Vehicle Control |
| 24 | 0.03 | 1 | 4 |
| 25 | 0.03 | 4 | 5 |

*This rabbit exhibited slight bleeding. (In many cases, in this model, when bleeding occurs no adhesions develop.)

This series of experiments indicates that the threshold dosage at which significant anti-adhesion effects begin to be noted in this model with suprofen sodium as the NSAID occurs when pumps containing a concentration of about 0.1 mg/ml of drug are used. Thus, on a weight basis, suprofen appears to be slightly more active than ibuprofen.

EXAMPLE 12

By a procedure analogous to that described above in Example 5, the 2 ml mini pump was used to deliver varying amounts of tolmetin. (The sodium dihydrate salt of tolmetin was used.) The concentrations of drug contained in the PBS (pH=7.4) varied from 0.01 mg/ml to 3.0 mg/ml. The treatment pumps contained the concentrations of tolmetin displayed below in Table VIII, and the control pumps contained vehicle only. The rabbits were sacrificed 7 days post-operatively, with results being displayed below in Table VIII:

TABLE VIII

| | Tolmetin, Dosage Response Studies | | |
|---|---|---|---|
| | Concentration of Tolmetin, | Evaluation | |
| Rabbit No. | mg/ml | Treatment | Vehicle Control |
| 1 | 3 | 1 | 1 |
| 2 | 3 | 1 | 1 |
| 3 | 3 | 1 | 5 |
| 4 | 3 | 1 | 1 |
| 5 | 3 | 1 | 3* |
| 6 | 1 | 1 | 4 |
| 7 | 1 | 1 | 5 |
| 8 | 1 | 3 | 5 |
| 9 | 1 | 1 | 3 |
| 10 | 1 | This rabbit died** | |
| 11 | 0.3 | 3 | 3 |
| 12 | 0.3 | 1 | 3* |
| 13 | 0.3 | 1 | 3 |
| 14 | 0.3 | 3 | 5 |
| 15 | 0.3 | 3 | 4 |
| 16 | 0.1 | 3 | 5 |
| 17 | 0.1 | 1 | 5 |
| 18 | 0.1 | 1 | 5 |
| 19 | 0.1 | 1 | 5 |
| 20 | 0.1 | This rabbit died (snuffles)*** | |
| 21 | 0.03 | 1 | 1 |
| 22 | 0.03 | 1 | 5 |
| 23 | 0.03 | 3 | 5 |
| 24 | 0.03 | 1 | 5 |
| 25 | 0.03 | 1 | 4 |
| 26 | 0.01 | 5 | 5 |
| 27 | 0.01 | 1 | 5 |
| 28 | 0.01 | 1 | 5 |
| 29 | 0.01 | 1 | 4 |
| 30 | 0.01 | 1 | 1 |

*Slight bleeding occurred.
**The cause of death was unknown, but there was no suggestion that it was drug-related.
***"Snuffles" is a virus-caused upper respiratory disease that affects rabbits. There is no suggestion that it was drug-related.

As can be seen from the data presented in Table VIII, tolmetin appears to be more effective, on a weight basis, than either IBF or suprofen in this rabbit model experiment. The threshold dosage in this experimental model, as indicated by the results reported above, was apparently less than the dosage administered to Rabbit Nos. 26–30, wherein the concentration of drug was 0.01 mg/ml.

EXAMPLE 13

The following is a typical preparation of a liposome (MLV) containing an NSAID (In this preparation, all materials and equipment used are sterile and pyrogen-free):

(a) Preparation of lipid film

L-alpha-distearoyl phosphatidylcholine ("DSPC"), 1.21 gm., and 0.29 gm. cholesterol (molar ratio of DSPC to cholesterol is 2:1), are dissolved in 45 ml. of chloroform. To this solution is added α-tocopherol so that the final concentration of α-tocopherol is 4% (w/v). The resulting solution is divided into nine 5 ml portions, and each such portion is placed in a 100 ml flask. The solvent is evaporated from each flask using a rotary vacuum evaporator. Sterility is maintained by attaching a 0.22 micron Millex filter to the air intake of the evaporator prior to flask removal. Sterile septa are placed on the flasks after solvent evaporation. The surface of each septum is wiped with 70% alcohol, and a 19 gauge sterile needle affixed to a 0.22 micron filter is passed through each septum. All flasks are then placed in a large vacuum desiccator and kept there overnight. Each flask contains about 167 mg. of lipid.

Alternatively, for purposes of scaling up, mixtures of DSPC, cholesterol, and α-tocopherol, in the proportions described above, are spray dried in a commercially available apparatus. The resulting powder may then be stored until needed for addition to NSAID solutions.

(b) Preparation of NSAID solution

The sodium salt of ibuprofen (Na-IBF), 0.202 gm., is dissolved in 40 ml of sterile, pyrogen-free water. The solution is then passed through a 0.22 micron Millex filter.

When NSAID solutions are prepared in a scaled-up mode, jacketed beakers with stir bars are connected to a circulating temperature regulated water reservoir and set on stir plates inside a sterile hood. Sterile phosphate buffered saline is prepared in the same sterile hood and appropriate volumes are added to the beakers, which are maintained at 65° C. To the pre-heated PBS is added the desired amount of NSAID, and the mixture is stirred to dissolve the drug.

(c) Preparation of MLV containing Na-IBF 3.9 Ml of the Na-IBF solution is injected into each flask containing lipid film. The flasks are vortex-stirred for 40 to 60 minutes in a 65° C. water bath under nitrogen. (The nitrogen purge is first passed through a 0.22 micron filter.) To the contents of each flask are added sterile, pyrogen-free PBS, and the flasks are centrifuged for 6 to 10 minutes at 15,000 rpm. This washing procedure is repeated for a total of five times to remove unencapsulated NSAID. The contents of the flasks are then combined and PBS (5mM PO$_4$ in 0.15 NaCl) is added to a total of 32 ml. The liposome suspension thus produced comprises MLV's of about 1 micron in size suspended in the PBS. It is storage stable for a period of several months.

To prepare drug-free controls, the procedure is repeated substituting pure water for the water/Na-IBF solution.

The procedure is repeated using (a) the free-acid form of IBF, and (b) the sodium salt of tolmetin. Similar results are obtained and liposome MLV's containing IBF or sodium tolmetin are produced.

In a scaled-up mode, once the NSAID is dissolved in the jacketed beaker at 65° C., an appropriate proportion of the spray-dried powder [prepared as described above in sub-paragraph (a)] is added. The beakers are then covered and the suspension is allowed to hydrate for 24 hours.

The hydrated suspension is apportioned into appropriate size vials. The vials are autoclaved for 40 minutes at 121° C. Sample vials are removed for analyses, and the remaining vials are stored at 5° C. The liposome-NSAID preparations are stable for several months under these conditions.

Analogous procedures would be employed to produce vesicles from phosphatidylcholines in which the fatty acid moieties were derived from other fatty acids, e.g., $C_{12}$ to $C_{24}$ fatty acids. $C_{14}$ to $C_{20}$ saturated fatty acids are preferred.

EXAMPLE 14

This experiment evaluated the efficacy of a liposome-/IBF combination to combat post-surgical adhesions. The procedure used was similar to that described above in Example 4 in which the treatment composition was applied to the site of surgical trauma in a single application, except that the untreated control sites in those rabbits that were given the liposome/IBF treatment were on the left-lateral peritoneal side-wall instead of being sited 1.5 to 2.0 centimeters inferior to the treatment sites in the right-lateral peritoneal side wall, and the wounding procedure described in Example 5 was used. The liposomes used in this example were DSPC/cholesterol MLV's, prepared in a manner analogous to that described above in Example 13. The treatment mixture consisted of 31 ml containing 1200 mg of MLV and 35 mg of the free acid form of IBF, suspended in 5 mM PBS. The vehicle control had the same composition, except that the IBF was omitted. Each rabbit received 10 ml of suspension, which amounted to 3.5 mg of IBF per rabbit. The treatment and vehicle control suspensions were dripped on the traumatized sites, as described above in Example 4. Three rabbits received the MLV/IBF treatment on the right side-wall site with the other site being untreated, and three rabbits received a vehicle control treatment (i.e., MLV without IBF) on the right side-wall site with no treatment on the other site. The rabbits were sacrificed 7 days post-operatively, and evaluated as described above. The results are displayed below in Table IX:

TABLE IX

| Rabbit No. | Liposome/Ibuprofen Studies | Site | |
|---|---|---|---|
| | Ibuprofen | Treated | Untreated |
| 1 | yes | 1 | 1 |
| 2 | yes | 1 | 1 |
| 3 | yes | 1 | 4 |
| 4 | no | 2 | 4 |
| 5 | no | 5 | 5 |
| 6 | no | 1 | 5 |

The experiment was repeated in exactly the same fashion, with the results as displayed below in Table X:

TABLE X

| Rabbit No. | Ibuorofen | Site | |
|---|---|---|---|
| | | Treated | Untreated |
| 1 | yes | 1 | 1 |
| 2 | yes | 1 | 1 |
| 3 | yes | 1 | 4 |
| 4 | no | 5 | 4 |
| 5 | no | 3 | 4 |
| 6 | no | 1 | 1* |

*This rabbit exhibited slight bleeding.

In the experiments reported above in Tables IX and X, the rabbits receiving treatment by the MLV/IBF combination were virtually free of adhesions, even on the sides that received no direct application of medicament. This is considered to be indicative of the fact that the medicament can migrate in the peritoneal cavity as a result of circulation of peritoneal fluid.

EXAMPLE 15

In this series of experiments, the procedure of Example 14 was repeated, with the following modifications: The liposomes that were used were DSPC/cholesterol MLV's prepared as described above in Example 13, and which contained Na-IBF. The control MLV's (two batches—"MLV-1" and "MLV-2") contained no drug. The drug-containing MLV's were mixed with the control MLV/s in varying proportions to obtain MLV's that contained varying amounts of NSAID. In Table XI, below, there is displayed the compositions of the drug-containing and the control liposomes:

TABLE XI

| | Liposome Composition | | | | |
|---|---|---|---|---|---|
| | Vol, ml | Lipid, mg/ml | Total Lipid, mg | Drug, mg/ml | Drug/Lipid, (by weight) |
| Control | | | | | |
| MLV-1 | 50 | 33 | 1675 | N/A | N/A |
| MLV-2 | 50 | 34 | 1710 | N/A | N/A |
| IBUPROFEN MLV | 50 | 33 | 1675 | 0.98 (49 gm) | 0.029 |

In Table XII, below, there is displayed the proportions of the drug-containing and control liposomes that were mixed together and then administered to the test rabbits in the manner described above in Example 14, along with the results of the evaluations of the rabbits seven days post-operatively:

TABLE XII

| | Na-IBF/MLV Evaluations | | | |
|---|---|---|---|---|
| Rabbit No. | IBF MLV, ml | Control MLV, ml | Evaluation | |
| | | | Treatment Site | Control Site |
| 1 | 10 | 0 | 1 | 1 |
| 2 | 10 | 0 | 3 | 3 |
| 3 | 10 | 0 | 1 | 1 |
| 4 | 3 | 7 | 1 | 1 |
| 5 | 3 | 7 | 1 | 4 |
| 6 | 3 | 7 | 1 | 5 |
| 7 | 3 | 7 | 1 | 4 |
| 8 | 1 | 9 | 1 | 1 |
| 9 | 1 | 9 | 1 | 1 |
| 10 | 1 | 9 | 1 | 1 |
| 11 | 1 | 9 | 1 | 1 |
| 12 | 0.3 | 9.7 | 1 | 3 |
| 13 | 0.3 | 9.7 | 1 | 3 |
| 14 | 0 | 10 | 4 | 5 |
| 15 | 0 | 10 | 5 | 3 |
| 16 | 0 | 10 | 3 | 3 |
| 17 | 0 | 10 | 4 | 5 |

TABLE XII-continued

Na-IBF/MLV Evaluations

| Rabbit No. | IBF MLV, ml | Control MLV, ml | Evaluation Treatment Site | Evaluation Control Site |
|---|---|---|---|---|
| 18 | 0 | 10 | 3 | 3 |

EXAMPLE 16

By a procedure analogous to that described above in Example 14, aqueous compositions including a surface active agent and the free acid form of tolmetin were applied to the treatment sites in the rabbit model. The aqueous compositions comprised various concentrations of "Tween 80", an ethoxylated sorbitan mono-oleate, in triple distilled water, and tolmetin at a concentration of either 1 or 2 mg/ml. The solutions were sterilized by passing them through a 0.22 micron filter. The tables below display the concentration of tolmetin and Tween 80, and the evaluations of the adhesions seven days post-operatively. In each case, 10 ml of the solution was dripped on the treatment site.

TABLE XIII

5 Wt. % Tween 80
1 mg/ml Tolmetin

| Rabbit No. | Evaluation Treatment Site | Control Site |
|---|---|---|
| 1 | 1 | 5 |
| 2 | 1 | 1 |
| 3 | 1 | 1 (Bleeding) |
| 4 | 1 | 1 |
| 5 (Control*) | 3 | 3 |
| 6 | 1 | 3 |
| 7 | 1 | 4 |
| 8 | 3 | 5 |
| 9 | 1 | 1 |
| 10 (Control*) | 4 | 3 |

*The control rabbits received no treatment.

TABLE XIV

20 Wt. % Tween 80
2 mg/ml Tolmetin

| Rabbit No. | Evaluation Treatment Site | Control Site |
|---|---|---|
| 1 | 1 | 5 |
| 2 | 3 | 5 |
| 3 | 1 | 4 |
| 4 | 3 | 1 |
| 5 (Control*) | 4 | 4 |
| 6 | 1 | 3 |
| 7 | 3 | 5 |
| 8 | 1 | 1 |
| 9 | 1 | 1 |
| 10 (Control*) | 5 | 5 |

*No Treatment

TABLE XV

20 Wt. % Tween 80
2 mg/ml Tolmetin

| Rabbit No. | Evaluation Treatment Site | Control Site |
|---|---|---|
| 1 | 1 | 5 |
| 2 | 1 | 1 (Bleeding) |
| 3 | 1 | 5 |
| 4 | 1 | 5 |
| 5 | 1 | 4 |
| 6 | 1 | 4 |
| 7 | 1 | 4 |
| 8 | 1 | 1 |

TABLE XVI 1 mg/ml Tolmetin Sodium[1]
No Tween

| Rabbit No. | Evaluation Treatment Site | Control Site |
|---|---|---|
| 1 | 3 | 5 |
| 2 | 4 | 3 |
| 3 | 1 | 3 |
| 4 | 3 | 4 |
| 5 | 3 | 3 |
| 6 | 4 | 3 |
| 7 | 1 | 3 |
| 8 | 3 | 5 |
| 9 (Control[2]) | 4 | 3 |

[1]The sodium salt was used because the free acid form is quite insoluble in pure water.
[2]Water only; no Tolmetin The free acid form of tolmetin, which is quite insoluble in water, was maintained in aqueous solution or colloidal suspension by the surface active agent.

Referring again to the question of the effective dose of NSAID when used in the invention, while no hard and fast numbers can be presented that will be applicable to all cases, the examples presented above can be referred to as a guide to determine the order of magnitude of drug to employ in particular cases. In PBS administered continually via the Alzet osmotic mini pump, the following dosages were found to be effective:

ibuprofen, 3 mg/ml, at a rate of 0.5 microliter/hr. (from Ex.6);

suprofen, 0.1 mg/ml, at a rate of 10 microliters/hr. (from Ex. 11); and tolmetin, 0.01 mg/ml, at a rate of 10 microliters/hr. (from Ex. 12).

Expressed in terms of mg/kg/day, and in terms of mg/day/cm$^2$ of traumatized tissue, these numbers are the following:

| | |
|---|---|
| ibuprofen | $18 \times 10^{-3}$ mg/kg/day |
| | $2.4 \times 1^{-3}$ mg/day/cm$^2$ |
| suprofen | $12 \times 10^{-3}$ mg/kg/day |
| | $1.6 \times 10^{-3}$ mg/day/cm$^2$ |
| tolmetin | $1.2 \times 10^{-3}$ mg/kg/day |
| | $0.16 \times 10^{-3}$ mg/day/cm$^2$ |

These calculations are carried out as follows (using the IBF numbers as illustrative): 0.5 microliter/hr. of solution containing 3 mg/ml equals $0.5 \times 10^{-6}$ liter/hr. $\times$ (3 mg/$10^{-3}$ liter). This reduces to $0.5 \times 3 \times 10^{-6}/10^{-3} = 1.5 \times 10^{-3}$ mg/hr. This equals $36 \times 10^{-3}$ mg/day or $18 \times 10^{-3}$ mg/kg/day (each rabbit weighs about 2 kg).

The area of traumatized tissue is about 15 cm$^2$, so the dose expressed in terms of mg/day/cm$^2 = 36/15 \times 10^{-3}$ mg/day/cm$^2$, or $2.4 \times 10^{-3}$ mg/day/cm$^2$.

Compared with the minimum recommended dose of 2.5 mg/kg/day (from the Singer patent cited above) for systemically administered IBF, the effective dose for topically administered IBF may be two to three orders of magnitude lower. Obviously, this greatly reduced dosage significantly reduces the chances for undesired side effects.

The minimum effective dose using an MLV or an aqueous composition containing a surface active agent as a carrier has apparently not been approached. However, it is noted from Example 15, Rabbit Nos. 12-13, that a total dose of about 0.3 mg of ibuprofen in an MLV carrier was effective. This number was calculated as follows:

0.98 mg/ml×0.3 ml/0.7 ml, equals 0.0278 mg/ml. Ten ml of this preparation was administered, so the total dosage was 0.3 mg or 0.15 mg/kg or 0.02 mg/cm$^2$. It would appear that an even lower concentration would be effective in this model.

In the Tween 80 solutions, the smallest amount of tolmetin applied was 10 mg (from the data presented in Table XIII). It would appear that an even smaller dosage administered in this manner would be effective.

A reasonable extrapolation of the data presented herein is that a minimum effective concentration for an NSAID preparation applied in a single dose would be between about 0.025 mg and 5 mg of NSAID per ml of total vehicle. (By "total vehicle" is meant an organic vehicle such as MLV or Tween 80 plus diluent such as water or PBS.)

Similarly, for an NSAID preparation that is administered continually, as by catheter, minimum effective concentrations of NSAID in total vehicle will usually be found within the range of from about 0.01 to about 10 mg/ml.

EXAMPLE 17

In this series, the uterine horn of New Zealand white female rabbits was used as the model for adhesion development. It is believed that the trauma induced in this type of surgical procedure is more apt to produce severe adhesions than any trauma ordinarily associated with surgery, and therefore this is a very severe test for evaluating the efficacy of a medicament in inhibiting the formation of post-surgical adhesions.

The rabbits were anesthetized using acelepromazine and ketamine, and then underwent a lower median laparotomy incision. The uterine horns were abraded with a gauze surgical sponge until punctate bleeding developed. The abrasion also removed the blood vessels that supplied the surface of the uterine horns with blood. Thus, the uterine horns were both abraded and devascularized.

Immediately after the uterine horns were devascularized and traumatized as described above, varying quantities of a MLV liposome (prepared by a procedure analogous to that described above in Example 13) containing the sodium salt of tolmetin were dripped on the traumatized site, and the rabbits were then closed. Seven days post-operatively, the rabbits were sacrificed and the development of adhesions was evaluated, with the results that are discussed below.

The liposomes were suspended in PBS, at a concentration of 40 mg of liposome per ml of suspension and 1.46 mg of tolmetin per ml of suspension. The results of the evaluations were as follows, with the quantities indicated being the volume of liposome suspension dripped on the site of surgical trauma:

10 ml—Scant adhesion
3 ml—Scant adhesion, but a few more than with the 10 ml dose. The adhesions were filmy
1 ml—Mild adhesions
Control—(no medicament)—Severe adhesions; essentially unable to open the rabbit without tearing adhesions which developed between the uterus and the bowel and between the uterus and the anterior peritoneal wall.

The above-described study was repeated several times with the liposome/tolmetin combination, with essentially the same results.

EXAMPLE 18

This example illustrates the preparation of aqueous phospholipid dispersions.

To 1487.5 ml of sterile pyrogen free water is added 51.0 grams of egg phosphatides. (Egg phosphatides are a 75/25, by weight, mixture of phosphatidyl choline and phosphatidyl ethanol amine lipids, with a mixture of fatty acids as isolated from an egg source.) The mixture is stirred by means of a magnetic stirrer to obtain a milky dispersion. The coarse milky dispersion is then further processed to reduce the dispersion particle size with a microfluidics M-110, a high energy dispersing apparatus. An organic acid, such as lactic acid, citric acid, or ascorbic acid is added, and the translucent dispersion is filtered through a 0.2 micron filter into sterile bottles which are capped with Teflon lined seals.

The amount of acid added varies, depending on the acid, such that the amount present will convert tolmetin sodium into its free acid form when the dispersion is mixed with an aqueous solution of tolmetin sodium just prior to use. The free acid form of tolmetin is substantially insoluble in pure water (as has been explained above), but it is solubilized in the lipid bilayer of the dispersed particles. Thus, 2.5 ml of a tolmetin sodium solution is added to 17.5 ml of the lipid dispersion, as described below, for a 20 ml final volume of NSAID-containing composition for use in the process of the invention.

TABLE XVII

| | For 20 ml Final Volume | | |
|---|---|---|---|
| Sample No. | Egg Phosphatides | Tolmetin Sodium | Acid |
| 18(a) | 0.6 gram | 49 mg, 0.155 mmol | Lactic |
| 18(b) | 0.6 gram | 49 mg, 0.155 mmol | Citric |
| 18(c) | 0.6 gram | 49 mg, 0.155 mmol | Ascorbic |
| 18(d) | 0.6 gram | 49 mg, 0.155 mmol | None |

49 mg of the dihydrate form of tolmetin sodium is equivalent to 40 mg of tolmetin acid, resulting in a dosage concentration equivalent to 2 mg/ml of tolmetin acid. The organic acids were used in the following quantities:

Lactic acid—21 mg or 0.233 mmol
Citric acid—29.9 mg or 0.155 mmol
Ascorbic acid—54.7 mg or 0.310 mmol These compositions were evaluated in the double uterine horn model described above in Example 17, with the results being displayed in Table XVIII, below:

TABLE XVIII

| Sample No. | Adhesion Rating |
|---|---|
| 18(a) | 1.5 |
| 18(a) | 1 |
| 18(a) | 2.5 |
| 18(a) | 2 |
| 18(a) | 2 |
| 18(b) | 2 |

TABLE XVIII-continued

| Sample No. | Adhesion Rating |
|---|---|
| 18(b) | 1 |
| 18(b) | 2 |
| 18(b) | 1 |
| 18(b) | 1.5 |
| 18(c) | 2 |
| 18(c) | 2 |
| 18(c) | 1.5 |
| 18(c) | 2.5 |
| 18(c) | 1.5 |
| 18(d) | 3.5 |
| 18(d) | 2 |
| 18(d) | 3 |
| 18(d) | 3 |
| 18(d) | 2.5 |
| Control, | 4 |
| No tolmetin | 4 |
|  | 3 |
| No tolmetin | 4 |
|  | 3 |

The rating system used in the double uterine horn model is the following:

0.5 —light, filmy pelvic adhesions involving only the bladder, typically only 1 or 2 small adhesions;
1 —light, filmy adhesions, not extensive although slightly more extensive than 0.5;
1.5 —the adhesions are slightly more extensive and are tougher than a 1 rating;
2 —tougher adhesions, a little more extensive, one uterine horn has filmy adhesions and the other has adhesions between either the bowel or the bladder, but not both;
2.5 —same as 2, except that adhesions to the uterine horn are not filmy
3 —tougher adhesions than 2, more extensive, both horns are attached to either the bladder or the bowel, some movement of the uterus possible;
3.5 —Same as 3 but both horns attached to both bladder and bowel;
4 —severe adhesions, both horns attached to both bladder and bowel, unable to move the uterus without tearing the adhesions.

While these ratings are somewhat subjective, the results reported herein are rated by the same persons using the same standards. Therefore, even though other persons might give different numerical ratings than those indicated herein, the comparisons given are valid.

EXAMPLE 19

In the experiments reported in this Example 19, the use of hyaluronic acid in combination with tolmetin to inhibit the formation of post-surgical adhesions was investigated. The double uterine horn adhesion model described above in Example 17 was employed. The treatment compositions evaluated were (a) an aqueous solution of sodium hyaluronate (in saline), (b) an aqueous solution of sodium tolmetin (in saline), and (c) an aqueous solution containing both sodium tolmetin and sodium hyaluronate (in saline). Tables XIX and XX, below, display the results of the evaluations in two separate series of experiments. The two controls were treated with saline only.

TABLE XIX

| Treatment | Adhesion Rating | Average |
|---|---|---|
| Tolmetin sodium solution, 2 mg/ml, 15 ml/rabbit | 2.0 1.5 2.5 2.5 3.0 | 2.3 |
| Tolmetin sodium solution, 10 mg/ml, 15 ml/rabbit | 2.5 3.0 4.0 1.5 4.0 | 3.0 |
| 1% Sodium hyaluronate solution, 15 ml/rabbit | 2.0 2.0 4.0 3.0 1.5 | 2.5 |
| 1% Na hyaluronate + 2 mg/ml Na tolmetin, 15 ml/rabbit | 1.5 2.0 1.0 0.5 2.0 | 1.4 |
| Control (saline only) | 3.0 4.0 4.0 3.0 4.0 | 3.6 |

TABLE XX

| Treatment | Adhesion Rating | Average |
|---|---|---|
| 1% Sodium hyaluronate solution, 15 ml/rabbit | 2.5 2.5 1.0 3.0 1.5 | 2.1 |
| 1% Na hyaluronate solution + 2 mg/ml Na tolmetin, 15 ml/rabbit | 1.5 0.5 1.5 1.0 1.0 | 1.1 |
| 1.5% Na hyaluronate solution + 2 mg/ml Na tolmetin, 15 ml/rabbit | 1.5 2.5 2.0 1.5 1.0 | 1.7 |
| 0.5% Na hyaluronate solution + 2 mg/ml Na tolmetin, 15 ml/rabbit | 1.5 1.5 2.5 1.5 0.5 | 1.5 |
| Tolmetin sodium solution, 2 mg/ml, 15 ml/rabbit | 2.0 1.5 2.5 2.5 2.5 | 2.2 |
| Tolmetin sodium solution, 10 mg/ml, 15 ml/rabbit | 3.0 2.5 2.0 2.5 3.0 | 2.6 |
| Control (saline only) | 4.0 4.0 4.0 3.5 3.5 | 3.8 |

The sodium hyaluronate employed was obtained from Kyowa Hakko (lot Nos. M8704 and M8708). The sodium hyaluronate was obtained as the sodium salt form as a sterile powder. The sterile powder was dissolved in saline and combined with a sterile solution of tolmetin sodium in saline to provide the appropriate final concentrations. The tolmetin sodium/saline solution was filtered and autoclaved (121° C. for 30 minutes). All of the work was carried out in a sterile field.

It is noted that sodium tolmetin solution (in the optimum concentration), alone, and hyaluronic acid, alone, are about equally efficacious in inhibiting the formation of adhesions. When the two are combined, the inhibiting effect on adhesion formation is significantly greater than either one used alone.

What is claimed is:

1. A process for inhibiting post-surgical adhesion formation in mammals which comprises the topical locally effective administration to the injured tissue surface site of surgical trauma of an effective amount of a composition including as an active ingredient a non-steroidal anti-inflammatory drug, such administration beginning after surgery and continuing for a period of time sufficient to inhibit the formation of post-surgical adhesions.

2. The process of claim 1 wherein the active ingredient is ibuprofen or a pharmaceutically acceptable salt or ester thereof.

3. The process of claim 1 wherein the active ingredient is suprofen or a pharmaceutically acceptable salt or ester thereof.

4. The process of claim 1 wherein the active ingredient is tolmetin or a pharmaceutically acceptable salt or ester thereof.

5. The process of claim 1 wherein said sterile composition includes hyaluronic acid or a pharmaceutically acceptable salt or ester thereof.

6. The process of claim 1 wherein said said sterile composition includes a phospholipid.

7. The process of claim 6 wherein said phospholipid is a phospholipid vesicle.

8. The process of claim 6 wherein the sterile composition comprises an aqueous mixture of a phospholipid, an organic acid, and tolmetin.

9. The process of claim 8 wherein said organic acid is ascorbic acid, lactic acid, or citric acid.

10. The process of claim 1 wherein said non-steroidal anti-inflammatory drug is contained in a controlled release carrier that released said drug over said period of time, wherein said carrier is an absorbable polymer.

11. The process of claim 10 wherein said absorbable polymer is a homopolymer or copolymer of lactic acid, glycolic acid, their cyclic dimer esters, or p-dioxanone.

12. The process of claim 11 wherein said polymer is in the form of microcapsules.

13. The process of claim 12 wherein said microcapsules include lecithin in an amount sufficient to enhance the ability of said microcapsules to adhere to the site of surgical trauma.

14. The process of claim 1 wherein the sterile composition comprises an aqueous composition including a surface active agent.

15. The process of claim 14 wherein the aqueous composition comprises an aqueous solution of ethoxylated sorbitan mono-oleate.

16. The process of claim 1 wherein said sterile composition is administered in a single dose, and wherein the concentration of active ingredient in said composition is at least about 0.025 to 5 milligrams per milliliter.

17. The process of claim 1 wherein said composition is administered continually over said period of time, and wherein the concentration of active ingredient in said composition is at least about 0.01 to 10 milligrams per milliliter.

18. A sterile aqueous composition including a surface active agent and a non-steroidal anti-inflammatory drug.

19. The sterile composition of claim 18 wherein the drug is ibuprofen, suprofen, tolmetin, or a pharmaceutically acceptable salt or ester thereof.

20. A sterile composition comprising an absorbable polymer microcapsule containing a non-steroidal anti-inflammatory drug.

21. The composition of claim 20 wherein the polymer is a homopolymer or copolymer of lactide, glycolide, or P-dioxanone.

22. The composition of claim 21 wherein the drug is ibuprofen, suprofen, tolmetin, or a pharmaceutically acceptable salt or ester thereof.

23. A sterile composition comprising an aqueous composition containing hyaluronic acid or pharmaceutically acceptable salt or ester thereof and a non-steroidal anti-inflammatory drug or pharmaceutically acceptable salt or ester thereof.

24. The sterile composition of claim 23 wherein the non-steroidal anti-inflammatory drug is tolmetin or pharmaceutically acceptable salt or ester thereof.

* * * * *

Notice of Adverse Decisions in Interference

In Interference No. 102,745, involving Patent No. 4,937,254, W. D. Sheffield, D. B. Johns, S. W. Shalaby, G. S. diZerega, METHOD FOR INHIBITING POST-SURGICAL ADHESION FORMATION BY THE TOPICAL ADMINISTRATION OF NON-STEROIDAL ANTI-INFLAMMATORY DRUG, final judgment adverse to the patentees was rendered Mar. 26, 1992, as to claims 23 and 24.

*(Official Gazette August 25, 1992.)*

REEXAMINATION CERTIFICATE (1770th)
United States Patent [19]
Sheffield et al.

[11] B1 4,937,254
[45] Certificate Issued   Aug. 11, 1992

[54] METHOD FOR INHIBITING POST-SURGICAL ADHESION FORMATION BY THE TOPICAL ADMINISTRATION OF NON-STEROIDAL ANTI-INFLAMMATORY DRUG

[75] Inventors: Warren D. Sheffield, Lebanon; Douglas B. Johns, Milford; Shalaby W. Shalaby, Lebanon, all of N.J.; Gere S. diZerega, Pasadena; LeRoy L. Richer, San Gabriel, both of Calif.

[73] Assignee: Ethicon, Inc., Somerville, N.J.

Reexamination Request:
No. 90/002,377, Jun. 25, 1991

Reexamination Certificate for:
Patent No.: 4,937,254
Issued: Jun. 26, 1990
Appl. No.: 148,464
Filed: Jan. 26, 1988

Related U.S. Application Data

[63] Continuation-in-part of Ser. No. 900,122, Aug. 25, 1986, abandoned, which is a continuation-in-part of Ser. No. 802,545, Nov. 27, 1985, abandoned.

[51] Int. Cl.$^5$ ............................................. A61K 31/74
[52] U.S. Cl. ............................... 424/497; 424/78.05; 514/420; 514/423; 514/576
[58] Field of Search ...................... 514/420, 576, 423; 424/78, 78.05, 497

[56] References Cited
U.S. PATENT DOCUMENTS
4,736,024   4/1988   della Valle et al. ................ 536/55.3

OTHER PUBLICATIONS
The Merck Index, p. 1362, item 9346, 10th Edition (1983).

Primary Examiner—Nathan M. Nutter

[57] ABSTRACT

Postsurgical adhesion formation is inhibited by the topical administration to the site of surgical trauma of a non-steroidal anti-inflammatory drug, preferably ibuprofen, suprofen, or tolmetin.

REEXAMINATION CERTIFICATE ISSUED UNDER 35 U.S.C. 307

AS A RESULT OF REEXAMINATION, IT HAS BEEN DETERMINED THAT:

The patentability of claims 1-22 is confirmed.

Claims 23 and 24 are cancelled.

* * * * *